United States Patent [19]

Takayama

[11] 4,298,260
[45] Nov. 3, 1981

[54] APPARATUS FOR ENDOSCOPIC PHOTOGRAPHY

[75] Inventor: Syuichi Takayama, Hachioji, Japan

[73] Assignee: Olympus Optical Company Ltd., Japan

[21] Appl. No.: 130,602

[22] Filed: Mar. 17, 1980

[30] Foreign Application Priority Data

Apr. 6, 1979 [JP] Japan .................................. 54/42254

[51] Int. Cl.³ ........................ G03B 7/083; A61B 1/04; G03B 15/03; G03B 17/18
[52] U.S. Cl. .................................. 354/50; 354/60 R; 354/62; 354/131; 354/173; 354/266; 354/289
[58] Field of Search ................. 354/50, 60 R, 62, 131, 354/266, 173, 289

[56] References Cited

U.S. PATENT DOCUMENTS 4,192,597 3/1980 Ting .................................. 354/62 X

FOREIGN PATENT DOCUMENTS 54-1985 1/1979 Japan .
54-1987 1/1979 Japan .

Primary Examiner—Michael L. Gellner
Attorney, Agent, or Firm—Ostrolenk, Faber, Gerb & Soffen

[57] ABSTRACT

An apparatus for endoscopic photography includes a camera and a light source unit which may be coupled to an endoscope to permit a picture to be taken of the interior of a coeliac cavity. An operating signal is converted into a high frequency signal by means of a conversion circuit which is disposed in one of the camera and the light source unit while a recovery circuit for recovering the operating signal from the high frequency signal is disposed in the other of the camera and the light source unit. In this manner, a communication of the operating signal between the camera and the light source unit is enabled through d.c. feed lines disposed within the endoscope which are utilized to feed a film winding d.c. motor.

8 Claims, 9 Drawing Figures

APPARATUS FOR ENDOSCOPIC PHOTOGRAPHY

BACKGROUND OF THE INVENTION

The invention relates to an apparatus for endoscopic photography, and more particularly, to an apparatus for endoscopic photography which is formed by a combination of a camera that is mounted on an endoscope and a light source unit connected to the latter.

As is well recognized, a combination of a photographic camera and a light source unit may be used to provide a photographing apparatus for an endoscope. Such apparatus includes an eyepiece assembly which is provided with a plurality of terminals for electrical interconnection including a power supply terminal which is utilized to feed a film winding motor disposed within the camera from a drive source located within the light source unit, a signal transmitting terminal which is effective to transmit a control signal from the camera to a diaphragm mechanism or the like disposed within the light source unit, and another signal transmitting terminal which may be used to transmit a signal from the light source unit to a display within the camera.

As is also well recognized, an endoscope includes a portion which is adapted to be inserted into a coeliac cavity. Such portion of the endoscope must be sterilized after it has been inserted into the cavity for purpose of observation or treatment. With the steam sterilization process which is currently available, the eyepiece assembly carrying the plurality of terminals is exposed to the hot steam concurrently with said portion of the endoscope for purpose of sterilization. Consequently, these terminals are susceptible to rust or corrosion resulting in poor electrical contact which may cause an unsatisfactory operation or a malfunctioning of the photographing apparatus associated with the endoscope. Since it is difficult to detect such poor contact beforehand, the failure to take a picture at a desired time may result.

SUMMARY OF THE INVENTION

In view of the foregoing, it is an object of the invention to provide an apparatus for endoscopic photography which comprises a high frequency conversion circuit which modulates a high frequency with a signal, and a superimposition circuit which superimposes the signal which modulated the high frequency on a d.c. voltage which is used to drive a film winding d.c. motor, both disposed in one of a photographic camera and a light source unit, and which also comprises a separator for separating the signal which modulated the high frequency from the d.c. voltage, and a signal recovery circuit which demodulates the separated signal, both disposed on the other of the camera and the light source unit, thereby allowing a signal transmission on a d.c. feed bus associated with the endoscope to enable the number of electrical contacts which must be provided on the eyepiece assembly of the endoscope to be minimized.

In an apparatus for endoscopic photography in which when a photographic camera is mounted on an endoscope and a light source unit is connected with the latter, a film winding d.c. motor disposed within the camera is connected with a d.c. source in the light source unit through a d.c. bus, the invention provides a high frequency conversion circuit which modulates a high frequency with a signal, and a superimposition circuit which superimposes the signal which modulated the high frequency on a d.c. voltage utilized for motor drive, both disposed on one of the camera and the light source unit, and also provides a separator for separating the modulated signal from the d.c. voltage, and a signal recovery circuit which demodulates the separated modulated signal, both disposed on the other of the camera and the light source unit. In this manner, a transmission of the signal is enabled between the camera and the light source unit through the d.c. feed bus.

In accordance with the invention, the d.c. feed bus disposed within the endoscope may include only two lead wires. Consequently, the number of terminals disposed in a connector assembly of the endoscope which is used for connection with the eyepiece and the light source unit is reduced to two. In this manner, the construction of the endoscope itself is simplified, and a maintenance of the terminals is facilitated during the time when the endoscope is sterilized, eliminating or minimizing the chance of occurrence of a poor contact.

DESCRIPTION OF PREFERRED EMBODIMENTS

Figure 1:
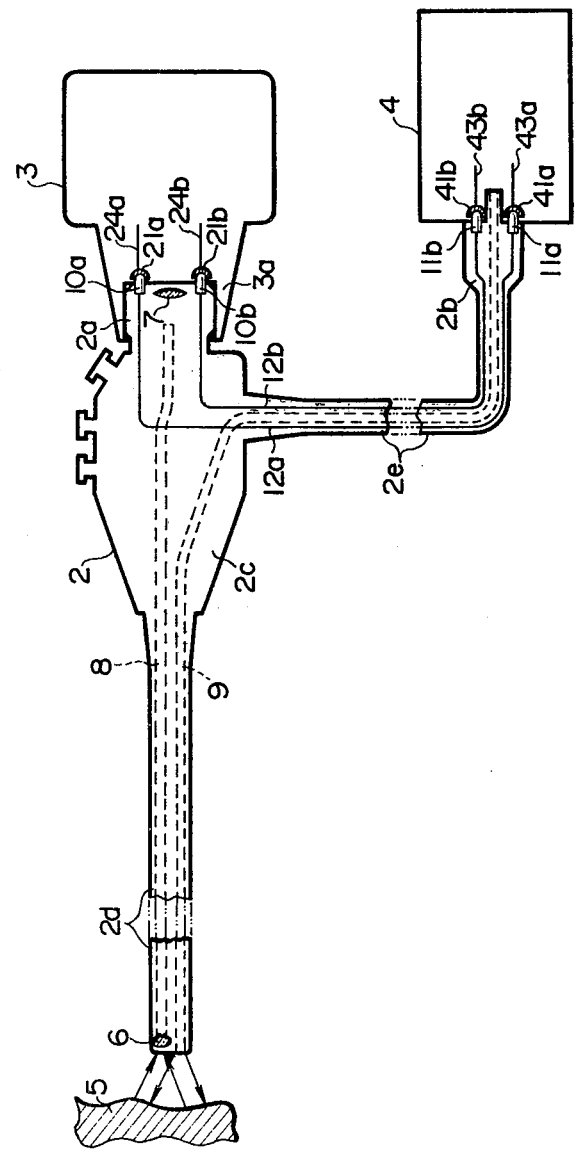
FIG. 1 is a schematic view of an apparatus for endoscopic photography according to one embodiment of the invention.

FIG. 1 shows an apparatus for endoscopic photography according to one embodiment of the invention. The apparatus 1 includes an endoscope 2, a photographic camera 3 having a mounting assembly 3a which is adapted to mate with an eyepiece assembly 2a of the endoscope, and a light source unit 4 to which a connector assembly 2b of the endoscope 2 is connected.

The endoscope 2 comprises a proximate end operator 2c which is located externally of the coeliac cavity for performing a variety of operations, a portion 2d connected to the left, as viewed in FIG. 1, of the proximate end operator 2c and adapted to be inserted into a coeliac cavity with its inner end being located in opposing relationship with the internal wall 5 of the cavity, the aforesaid eyepiece assembly 2a projecting from the right-hand, as viewed in FIG. 1, of the proximate end operator 2c, a coupling tube 2e extending from the bottom, as viewed in FIG. 1, of the operator 2c and extending to the light source unit 4, and the connector assembly 2b provided on the other end of the coupling tube 2e. Also disposed within the endoscope 2 are an objective lens 6 which is disposed on the distal end of the portion 2d, a bundle of optical fibres 8 which serves as an image guide to provide an optical coupling between the objective lens 6 and an eyepiece 7 disposed in the eyepiece assembly 2a, another bundle of optical fibres 9 which serves as a light guide to provide an optical coupling between the distal end of the endoscope portion 2d and the connector assembly 2b by passing through the endoscope portion 2d, the proximate end operator 2c, the coupling tube 2e and the connector assembly 2b, a pair of feed terminals 10a, 10b disposed in the outer surface of the eyepiece assembly 2a, a pair of feed terminals 11a, 11b disposed on the outer end of the connector assembly 2b, a pair of supply buses 12a, 12b providing an interconnection between the terminals 10a, 11a and between the terminals 10b, 11b, respectively.

Figure 2:
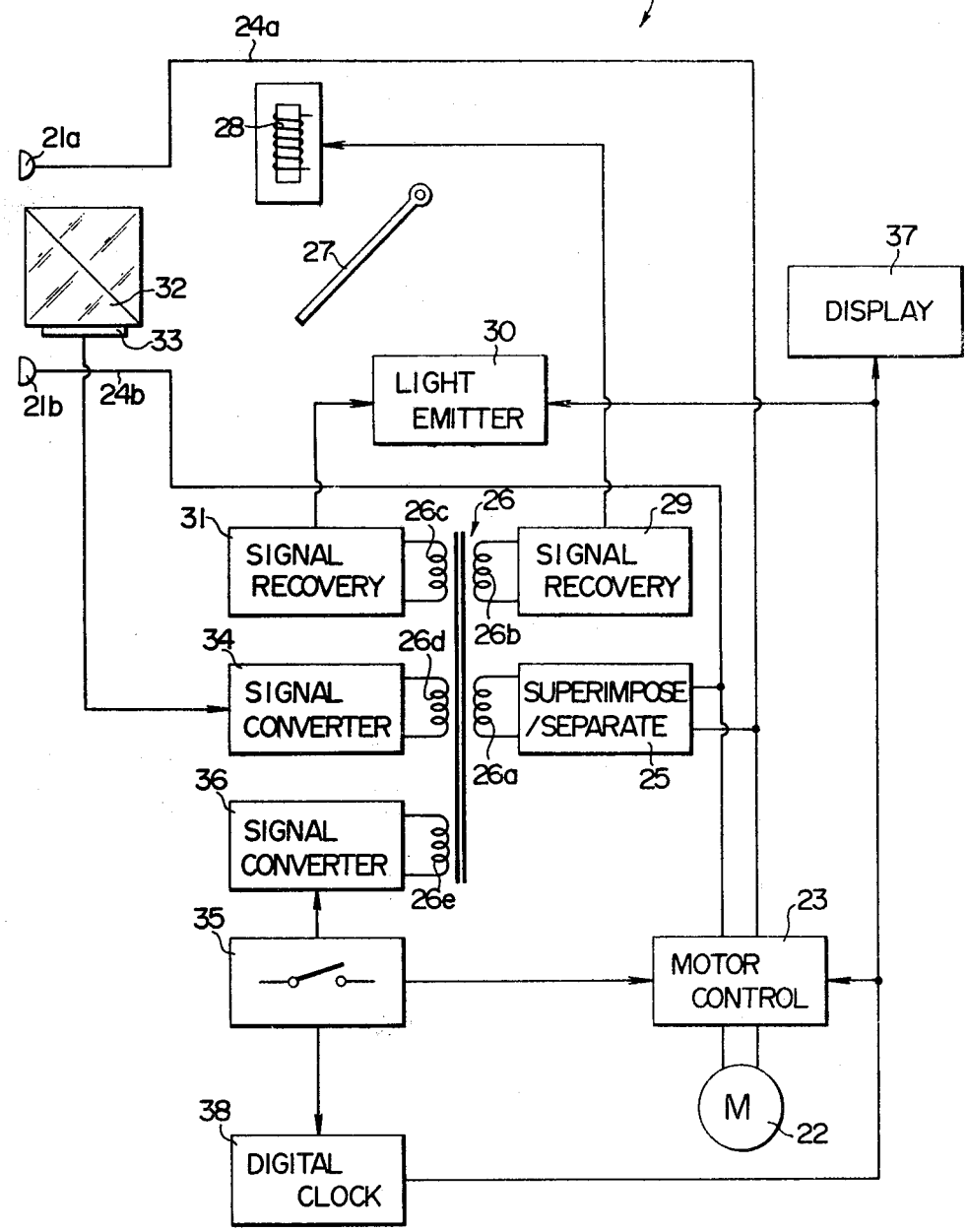
FIG. 2 is a block diagram of an electrical circuit which is disposed in the camera of the apparatus shown in FIG. 1.

As shown in FIG. 2, the camera 3 includes a pair of power terminals 21a, 21b which are adapted to mate with the feed terminals 10a, 10b to be fed therefrom as the camera 3 is mounted on the eyepiece assembly 2a of the endoscope 2. A film winding d.c. motor 22 is electrically driven by a power fed from the power terminals 21a, 21b and is controlled by, a motor control circuit 23. A pair of feed lines 24a, 24b interconnect the motor control circuit 23 with the power terminals 21a, 21b. A superimposition and separator circuit 25 is connected across the feed lines 24a, 24b and may be formed by a filter circuit or the like. A coupling transformer 26 has one of its coils 26a connected with the superimposition and separator circuit 25. An electromagnet assembly 28 permits a release operation of a mirror shutter 27, and is controlled by a signal recovery circuit 29 connected to another one of the coils 26b of the coupling transformer 26 and is formed by a demodulator circuit to supply an operating signal to the electromagnet assembly 28. A light emitter assembly 30 permits the entry of data such as a photographing date or the number of film frames onto a film and receives an operating signal from signal recovery circuit 31 which is connected with a further one of the coils 26c of the coupling transformer 26 and formed by a demodulator. A light receiving element 33 is disposed on the lower surface of a half prism 32 which is disposed in a light path in front of the mirror shutter 27 for effecting photometry in order to achieve an automatic exposure control. A signal conversion circuit 34 formed by a modulator connected with yet another one of the coils 26d of the coupling transformer 26 receive an output from the light receiving element 33 and transmits an automatic exposure control signal. A synchro switch 35 is adapted to be closed in response to the depression of a shutter release button, not shown and applies a close signal to another signal conversion circuit 36 connected to a still further one of the coils 26e of the coupling transformer 26. Circuit 36 is formed by a high frequency modulator to provide a synchro switch close signal. A display 37 includes segment-shaped elements such as liquid crystal display elements or light emitting diodes for displaying a photographing date or the number of film frames externally of the camera 3. A digital clock circuit 38 supplies a clock signal to the display 37, the light emitter assembly 30 and the motor control circuit 23. The synchro switch 35 supplies its close signal to the motor control circuit 23 and the digital clock circuit 38 as well as the signal conversion circuit 36. It is to be noted that the superimposition and separator circuit 25 is electromagnetically coupled through the coupling transformer 26 with the signal recovery circuits 29, 31 and the signal conversion circuits 34 and 36. A high frequency signal supplied to the superimposition and separator circuit 25 may be demodulated by the signal recovery circuits 29, 31. Alternatively, the high frequency signal which is modulated by the signal conversion circuits 34, 36 may be delivered by the superimposition and separator circuit 25 to the feed lines 24a, 24b. The individual circuits 29, 31, 34 and 36 demodulate or modulate different high frequency bands, which define separate channels. In this manner, interferences between high frequency signals which are demodulated or modulated by the respective circuits 29, 31, 34 and 36 are avoided, insuring that they can be distinguished from each other.

Figure 3:
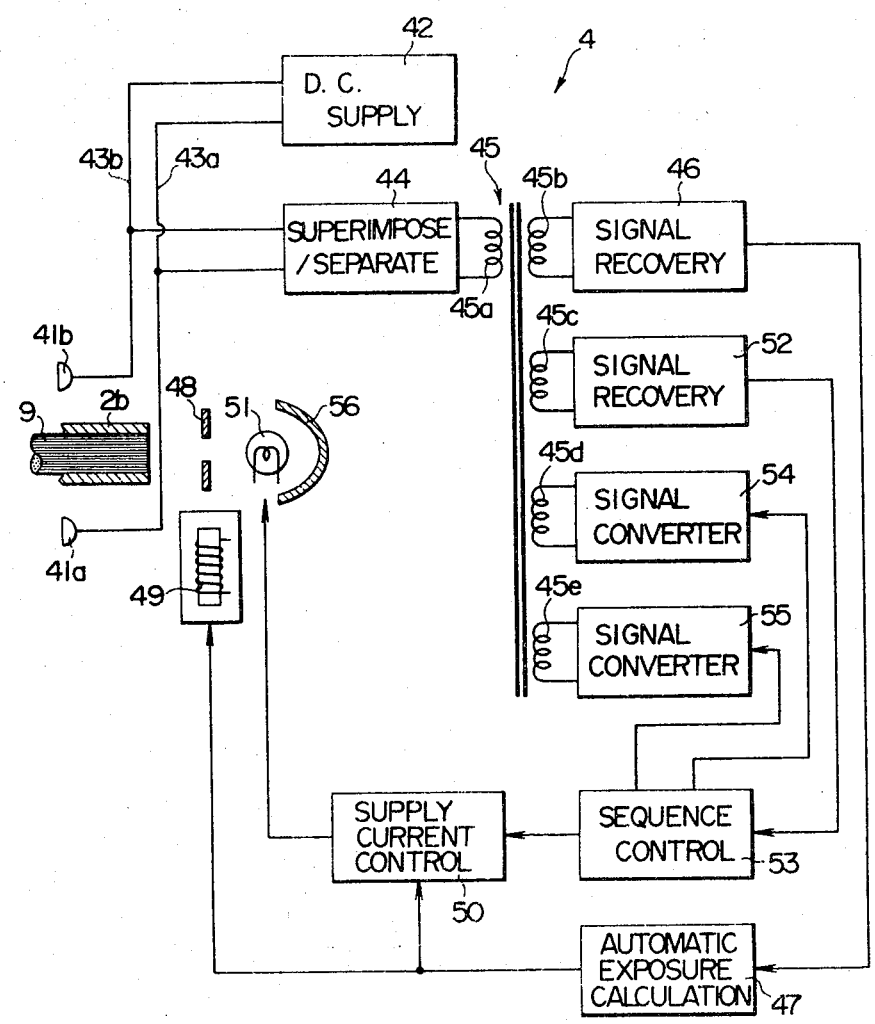
FIG. 3 is a block diagram of an electrical circuit disposed in the light source unit of the apparatus shown in FIG. 1.

As shown in FIG. 3, the light source unit 4 includes power output terminals 41a, 41b which mate with the feed terminals 11a, 11b to supply d.c. power to the motor 22 when the unit 4 is coupled to the connector assembly 2b of the endoscope 2. A power supply circuit 42 is connected to output terminals 41a, 41b by feed lines 43a, 43b. A superimposition and separator circuit 44 is formed by a filter circuit connected across the lines 43a, 43b. A coupling transformer 45, having a coupling coil 45a is connected to the superimposition and separator circuit 44. A signal recovery circuit 46 is connected to another one of coils 45b of the transformer 45 and demodulates a high frequency signal which has been modulated by the automatic exposure signal conversion circuit 34 of the camera 3. An automatic exposure calculation circuit 47 receives an automatic exposure signal which is demodulated by the signal recovery circuit 46. An electromagnet assembly 49 is responsive to an output from the calculation circuit 47 to open or close a diaphragm mechanism 48. A supply current control circuit 50 receives an output from the calculation circuit 47 and controls the brightness of a light 51. A synchronizing switch close signal recovery circuit 52 is connected to a further one of coils 45c of the coupling transformer 45 and demodulates a high frequency signal which has been modulated by the synchronizing switch close signal conversion circuit 36 of the camera 3. A sequence control circuit 53 receives a synchronizing switch close signal which has been demodulated by the recovery circuit 52. A conversion circuit 54 is connected to yet another one of coils 45d of the transformer 45 and is formed by a modulator which modulates a high frequency with an operating signal associated with the light emitter assembly 30 of the camera 3 which is generated by the sequence control circuit 53. Another conversion circuit 55 is connected to a yet further one of coils 45e of the transformer 45 and is formed by a modulator which modulates a high frequency with a shutter release signal produced by the sequence control circuit 53. The superimposition and separator circuit 44 is electromagnetically coupled with the signal recovery circuits 46, 52 and signal conversion circuits 54, 55 through the coupling transformer 45, whereby high frequency signals supplied to the superimposition and separator circuit 44 may be demodulated by the signal recovery circuits 46, 52 or high frequency signals which have been modulated by the signal conversion circuits 54, 55 may be delivered through the feed lines 43a, 43b. As mentioned previously, the respective circuits 29, 31, 34 and 36 of the camera 3 demodulate or modulate mutually different high frequency bands, and in the corresponding manner, the individual circuits 55, 54, 46 and 52 of the light source unit 4 demodulate or modulate mutually different frequency bands, thus avoiding interference therebetween. In FIG. 3, numeral 56 represents a reflector associated with light 51.

In operation, the connector assembly 2b of the endoscope 2 is connected to the light source unit 4, and the camera 3 is mounted on the eyepiece assembly 2a. Then, the feed terminals 11a, 11b are connected to the power output terminals 41a, 41b while power terminals 21a, 21b are connected to feed terminals 10a, 10b, respectively, as shown in FIG. 1. In this manner, the electrical circuits of the camera 3 and the light source unit 4 are connected together through the d.c. feed buses 12a, 12b. Hence, it is possible to feed the motor 22 from the d.c. power supply circuit 42 within the light source unit 4 through the motor control circuit 23. The provision of the superimposition and separator circuits 25, 44 and the coupling transformers 26, 45 permits a bilateral communication of signals between the camera 3 and the light source unit 4. On the other hand, the light source unit 4 and the camera 3 are optically coupled together through the light guide 9 and the image guide 8 of the endoscope 2.

By viewing a viewfinder, not shown, of the camera, a desired area within the coeliac cavity may be brought into the field of sight. A shutter release button, not shown, may then be depressed to close the synchronizing switch 35. A close signal which indicates the closure of the synchronizing switch 35 is applied to the signal conversion circuit 36 which modulates the close signal with a high frequency carrier signal. The modulated signal is fed to the superimposition and separator circuit 25 which superimposes the modulated signal on a d.c. current on the feed lines 24a, 24b so as to deliver it to the light source unit 4 through the d.c. feed buses 12a, 12b. Within the light source unit 4, the superimposition and separator circuit 44 separates the modulated synchronizing switch close signal from the d.c. component. The modulated close signal is demodulated by the signal recovery circuit 52 and then fed through the sequence control circuit 53 to the supply current control circuit 50. In response to the synchronizing switch close signal, the control circuit 50 increases supply current to the light 51, thus increasing the amount of light which irradiates an object being photographed. When the increased amount of light is projected into the coeliac cavity through the light guide 9, the resulting increased brightness of the object being photographed is reflected into the image guide 8 and then into the camera 3. Part of light from the object which is introduced into the camera 3 transmits through the half prism 32 to reach the film surface to cause an exposure thereof, since the mirror shutter 27 moves up in response to the depression of the shutter release button, as will be further described later. Another part of the light is reflected by the half prism 32 to impinge on the photometric, photoelectric transducer element 33, which determines the brightness of the object to produce an automatic exposure signal which is fed to the signal conversion circuit 34. The automatic exposure signal is used to modulate a high frequency signal in the conversion circuit 34, and then fed to the superimposition and separator circuit 25, which superimposes the modulated signal on a motor drive d.c. current on the feed lines 24a, 24b. In this manner the modulated signal is fed to the light source unit 4 through the d.c. feed buses 12a, 12b. Within the light source unit 4, the modulated signal is separated from the d.c. component by the superimposition and separator circuit 44 and applied to the coupling coil 45a. The signal recovery circuit 46 which is tuned to the corresponding frequency derives it through the coupling coil 45b and demodulate it to recover the automatic exposure signal, which is then fed to the exposure control calculation circuit 47. The calculation circuit 47 activates the electromagnet assembly 49 after an exposure period which is determined by a calculation of the signal, thus causing the diaphragm mechanism 48 to close. Simultaneously, calculation circuit 47 operates the supply current control circuit 50 to reduce the current flow to the light 51, thus automatically controlling the amount of light so that a proper exposure is achieved for the camera 3.

In addition to being applied to the supply current control circuit 50, the close signal indicative of the closure of the synchronizing switch 35 is applied by the sequence control circuit 53 to the signal conversion circuit 55 as a shutter release signal and also to the signal conversion circuit 54 as an operating signal which activates the light emitter assembly 30 for purpose of data entry. In response thereto, these signal conversion circuits 55, 54 convert the respective signal to a high frequency signal, which is then coupled through the transformer 45 and the superimposition and separator circuit 44 and the d.c. feed buses 12a, 12b to the camera 3. When the shutter release signal and the operating signal are applied to the camera 3, the superimposition and separator circuit 25 operates to separate these signals and to supply them to the individual signal recovery circuits 29, 31, which recover the individual signals and feed them to the electromagnet assembly 28 and the light emitter assembly 30, respectively. As described previously, the electromagnet assembly 28 releases the mirror shutter 27 and the light emitter assembly 30 emits light to effect data entry onto the film in response to these signals.

The close signal indicative of the closure of the synchronizing switch 35, which is produced in response to the depression of the shutter release button, is also fed to the motor control circuit 23 and the digital clock circuit 38. The output of the digital clock circuit 38 is also fed to the motor control circuit 23. Hence, after the closure of the synchronizing switch 35 when the mirror shutter has terminated its upward and downward movement, a gate within the motor control circuit 23 is enabled to permit the motor 22 to be fed from the power supply circuit 42 of the light source unit 4 through the d.c. feed buses 12a, 12b, thus winding up the film through one frame upon completion of a photographing operation.

In the manner mentioned above, a series of operations associated with a single depression of the shutter release button including a shutter release, an automatic exposure control, an exposure of the film surface and a film winding operation are terminated, whereby the apparatus 1 for endoscopic photography returns to its normal condition in preparation to a next photographing operation.

It is to be noted that since the digital clock circuit 38 is also connected to the display 37, data such as a photographing date which is entered onto the film by the light emitter assembly 37 can be externally recognized.

Figure 4:
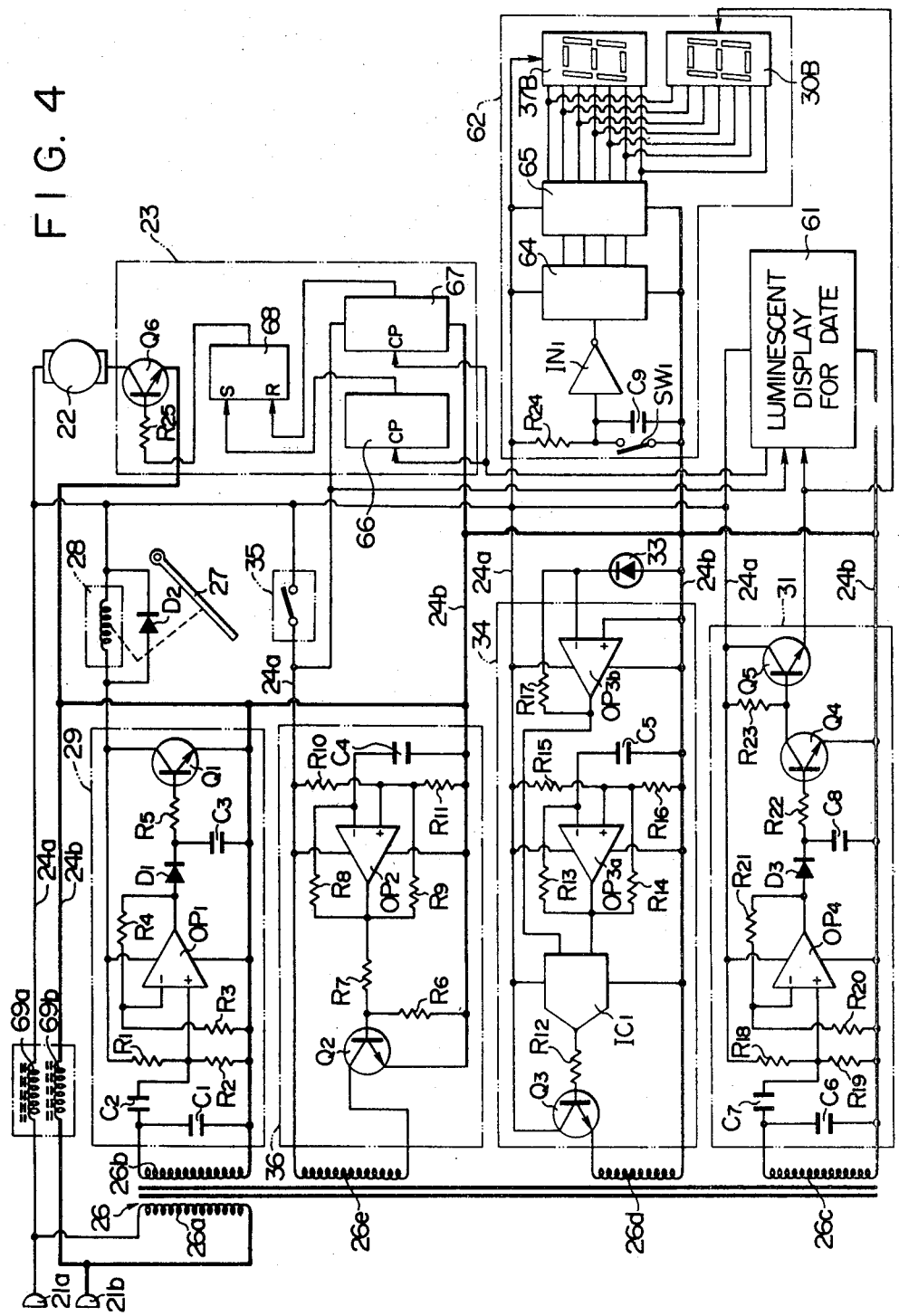
FIG. 4 is a circuit diagram of one specific example of the electrical circuit of the camera shown in FIG. 2.
Figure 6:
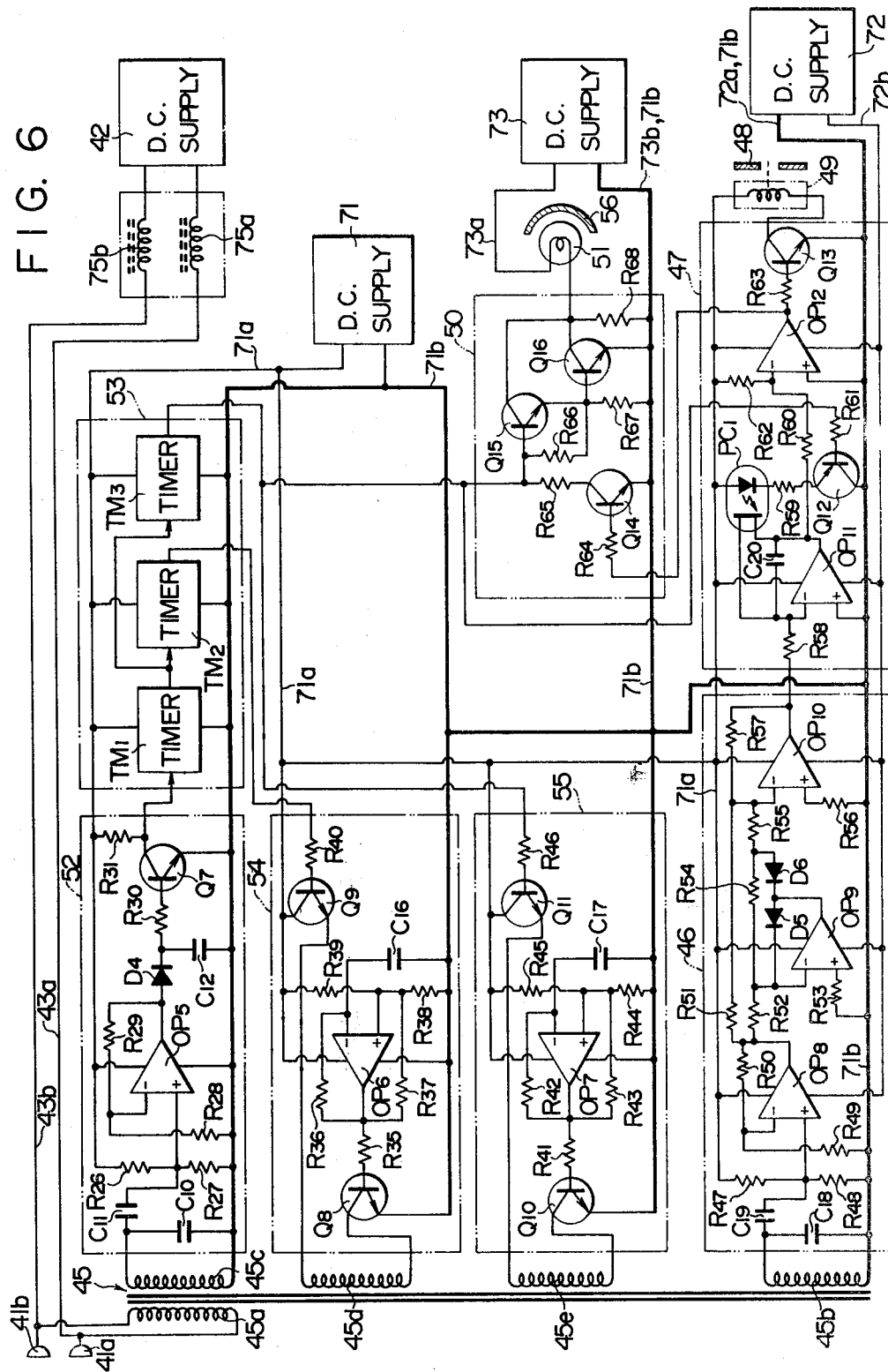
FIG. 6 is a circuit diagram of a specific example of the electrical circuit of the light source unit shown in FIG. 3.

FIGS. 4 and 6 show one specific example of the electrical circuit of the camera and the light source unit shown in FIGS. 2 and 3, respectively. Referring to FIG. 4 which shows a specific electrical circuit of the camera 3, the signal recovery circuit 29 which is utilized to operate the electromagnet comprises a resonance capacitor $C_1$, an input coupling capacitor $C_2$, an a.c. amplifying operational amplifier $OP_1$, a rectifying diode $D_1$, a smoothing capacitor $C_2$, a transistor $Q_1$ which controls the drive to the electromagnet assembly 28, and resistors $R_1$–$R_5$. The resonance capacitor $C_1$ is connected in shunt with coil 26b of the coupling transformer 26, forming therewith a resonance circuit which is tuned to an a.c. input of a given high frequency $f_1$. One end of the capacitor $C_1$ is connected to the feed line 24b while the other end is connected to one end of the input coupling capacitor $C_2$, the other end of which is connected to the junction between resistors $R_1$ and $R_2$. the junction is also connected to a non-inverting input of the operational amplifier $OP_1$. The resistors $R_1$ and $R_2$ form a series connected voltage divider, with one end of resistor $R_1$ connected through the electromagnet assembly 28 to the feed line 24a and the other end of resistor $R_2$ connected to feed line 24b. The operational amplifier $OP_1$ is connected across the feed lines 24a, 24b, and has its inverting input connected to the junction between resistors $R_3$ and $R_4$ which are connected in series across its output and the feed line 24b. The output of the operational amplifier $OP_1$ is connected to the anode of the rectifying diode $D_1$, the cathode of which is connected through the smoothing capacitor $C_3$ to the feed line 14b and also connected through resistor $R_5$ to the base of the transistor $Q_1$. The transistor $Q_1$ comprises an NPN transistor having its collector connected through the electromagnet assembly 28 to the feed line 24a and its emitter connected to the feed line 24b.

The signal recovery circuit 29 responds to a shutter release signal of frequency $f_1$ from the shutter release signal conversion circuit 55 of the light source unit 4, which is specifically shown in FIG. 6, by selecting an a.c. input developed across the coil 26b of the transformer 26 by the resonance circuit which the coil forms together with the capacitor $C_1$. After the signal is amplified by the operational amplifier $OP_1$, it is rectified by the diode $D_1$ and smoothed by the capacitor $C_3$ to be fed to the transistor $Q_1$, turning it on to energize the electromagnet assembly 28. When the electromagnet assembly 28 is energized, the mirror shutter 27 is driven to move up, whereby the exposure of the film surface to an image of the object being photographed is initiated. Diode $D_2$ connected in shunt with the electromagnet assembly 28 functions to suppress a counter electromotive force developed across the latter when it is deenergized.

The synchronizing switch close signal conversion circuit 36 comprises a power amplifier transistor $Q_2$, an oscillation operational amplifier $OP_2$, resistors $R_6$–$R_{11}$ and capacitor $C_4$. The transistor $Q_2$ comprises an NPN transistor having its collector connected to one end of the coil 26e which has its other end connected through the synchronizing switch 35 to the feed line 24a, and has its emitter connected to the feed line 24b. The base of the transistor $Q_2$ is connected through resistor $R_6$ to the feed line 24b, and also connected through resistor $R_7$ to the output of the operational amplifier $OP_2$. The operational amplifier $OP_2$ is connected through the synchronizing switch 35 across the feed lines 24a, 24b, and has its inverting input connected through resistor $R_8$ to its output and also connected through capacitor $C_4$ to the feed line 24b. The non-inverting input of the operational amplifier $OP_2$ is connected through resistor $R_9$ to its output and also connected to the junction between resistors $R_{10}$ and $R_{11}$. The series combination of the resistors $R_{10}$, $R_{11}$ is connected across the feed lines 24a, 24b in series with the synchronizing switch 35.

In response to the closure of the synchronizing switch 35, the oscillator circuit comprising the operational amplifier $OP_2$ begins to oscillate at a given high frequency $f_2$, and the resulting oscillation output is amplified by the transistor $Q_2$ before it is applied to the coil 26e of the transformer 26.

The automatic exposure signal conversion circuit 34 comprises a power amplifier transistor $Q_3$, a multiplier circuit formed by an integrated circuit $IC_1$, an oscillation operational amplifier $OP_{3a}$, d.c. amplifying operational amplifier $OP_{3b}$, resistors $R_{12}$–$R_{17}$ and capacitor $C_5$. The transistor $Q_3$ comprises an NPN transistor having its collector connected to the feed line 24a and its emitter connected to the feed line 24b through the coil 26d of the transformer 26. The base of the transistor $Q_3$ is connected through resistor $R_{12}$ to the output of the multiplier circuit $IC_1$. The multiplier circuit $IC_1$ is connected across the feed lines 24a, 24b, and has its one input connected to the output of the operational amplifier $OP_{3b}$ and its other input connected to the output of the operational amplifier $OP_{3a}$. The oscillation operational amplifier $OP_{3a}$ is also connected across the feed lines 24a, 24b, and has its inverting input connected through resistor $R_{13}$ to its output and also connected through capacitor $C_5$ to the feed line 24b. The non-inverting input of the operational amplifier $OP_{3a}$ is connected through resistor $R_{14}$ to its output and also connected to the junction between resistors $R_{15}$, $R_{16}$ which are connected in series across the feed lines 24a, 24b. The d.c. amplifying operational amplifier $OP_{3b}$ is connected across the feed lines 24a, 24b, and has its inverting input connected through resistor $R_{17}$ to its input and also connected to the feed line 24b through the photometric element or photodiode 33 which is reversely poled. The non-inverting input is connected to the feed line 24b.

In the operation of the automatic exposure signal conversion circuit 34, a photocurrent produced by the photoelectric transducer element 33 is subject to a d.c. amplification by the operational amplifier $OP_{3b}$, the output of which is used to modulate, by superimposition, an oscillation output of the operational amplifier $OP_{3a}$ having a given high frequency $f_3$, by means of the multiplier circuit $IC_1$. The modulated output is subject to a power amplification by the transistor $Q_3$ before it is supplied to the coil 26d of the transformer 26.

The signal recovery circuit 31 associated with the light emitter assembly comprises a resonance capacitor $C_6$, an input coupling capacitor $C_7$, an a.c. amplifying operational amplifier $OP_4$, a rectifying diode $D_3$, a smoothing capacitor $C_8$, a compounded pair of transistors $Q_4$, $Q_5$ which controls the drive to the light emitter assembly 30, and resistors $R_{18}$–$R_{23}$. It will be noted that the signal recovery circuit 31 is constructed in generally the same manner as the signal recovery circuit 29 associated with the electromagnet assembly, except that voltage divider resistor $R_{18}$ and the power supply terminal of the a.c. amplifying operational amplifier $OP_4$ are directly connected to the feed line 24a and that the transistor $Q_4$ of NPN type has its collector connected to the base of the transistor $Q_5$ of PNP type which has its emitter connected to the feed line 24a and its collector connected to an output terminal of the circuit 31 for connection with a luminescent display 61, to be described later, which displays a photographing date, as well as a light emitting diode assembly 30B which is used for the entry of the number of film frames. It will be noted that resistor $R_{23}$ is connected across the base and emitter of transistor $Q_5$.

In the operation of the signal recovery circuit 31, the conversion circuit 54, to be described later in connection with FIG. 6 and which produces a signal to energize the light within the light source unit 4, produces a signal of a given high frequency $f_4$ which is coupled to the coil 26c. The resulting a.c. input is picked up by the capacitor $C_6$ and amplified by the operational amplifier $OP_4$. Subsequently it is rectified by the diode $D_3$ and smoothed by the capacitor $C_8$ to be applied to the transistors $Q_4$, $Q_5$, thus turning them on to cause an illumination of the light emitter assembly 30 for purpose of data entry.

The light emitter assembly 30 and the display 37 shown in block form in FIG. 2 comprises a luminescent display 61 for displaying a photographing date, and a luminescent display 62 for displaying the number of film frames, as illustrated in FIG. 4.

Figure 5:
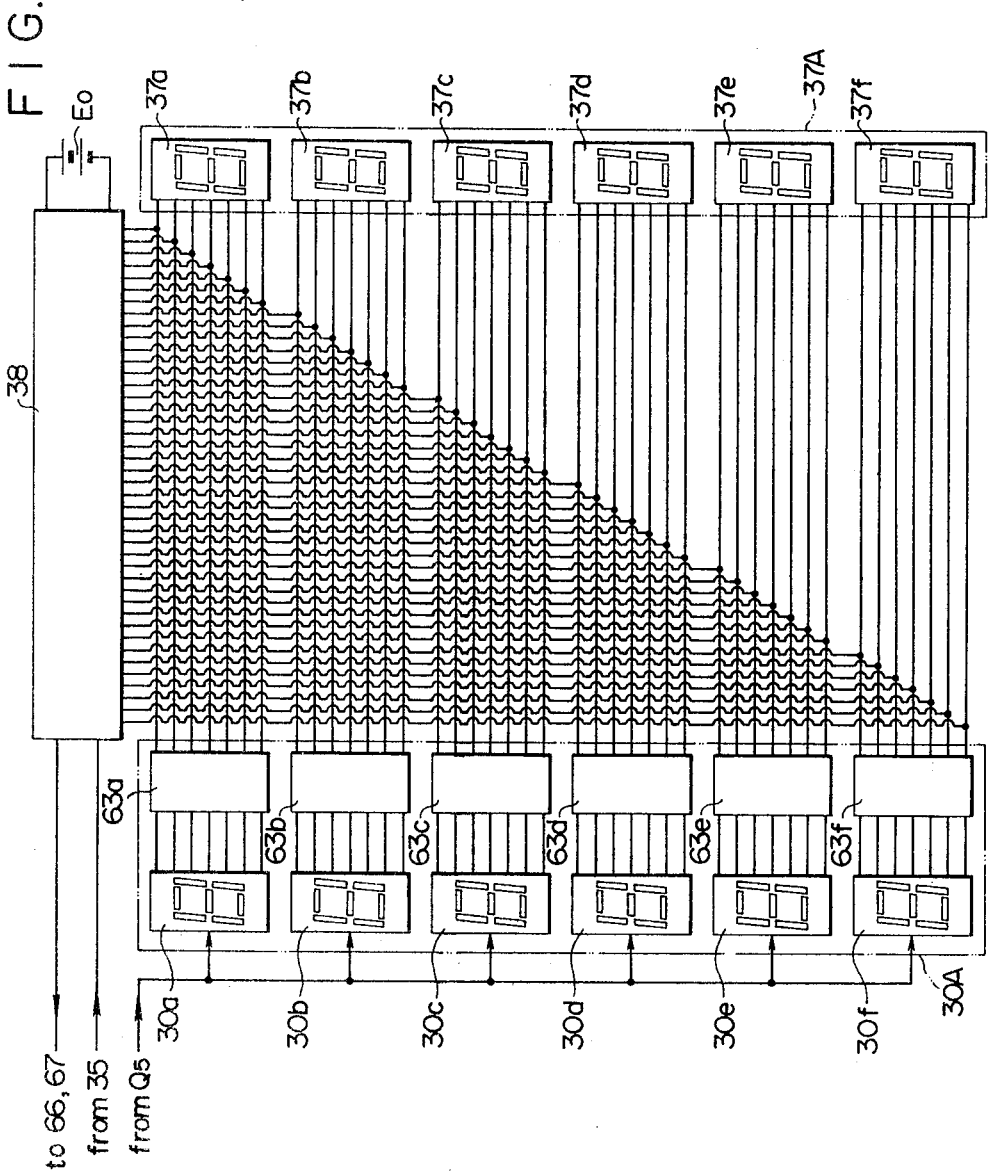
FIG. 5 is a circuit diagram showing the detail of a photographing date luminescent display which is shown in the electrical circuit of FIG. 4.

As shown in detail in FIG. 5, the luminescent display 61 comprises a light emitter assembly 30A which is used for entry of a photographing date, a display 37A which displays a photographing date, and the digital clock circuit 38 which is well known in itself. The assembly 30A includes six 7-segment light emitting diode elements 30a–30f which indicate numerals, and buffer circuits 63a–63f which drive these elements. The display 37A includes six 7-segment liquid crystal elements 37a–37f which also indicate numerals. The clock circuit 38 is formed by a large scale integrated circuit which drives the liquid crystal elements. The timing function of the clock circuit 38 is achieved by normally energizing it from a power source $E_O$ which is internally housed within the camera 3. A photographing date which is established as a result of a counting operation by the circuit 38 is outputted on $7 \times 6 = 42$ drive control lines, from which drive control signals for the liquid crystal elements 37a–37f are derived. It will be noted that a set of seven drive control lines is connected to each of the elements 37a–37f, and is also connected to each of the diode elements 30a–30f through the respective buffer circuits 63a–63f. Each of the light emitting diode elements 30a–30f is connected to the collector of the transistor $Q_5$, and is thus fed from the feed line 24a when the transistor $Q_5$ is turned on. It will be noted that the buffer circuits 63a–63f are connected across the feed lines 24a, 24b. The liquid crystal elements 37a–37f are also connected with the feed line 24a, but the connection is not illustrated in FIG. 5. On the other hand, the clock circuit 38 is connected to one terminal of the synchronizing switch 35, and is responsive to a close signal from the switch 35 to produce count pulses of a frequency such as 32 Hz, for example, which are fed to a decimal counter 66 and another counter 67 having a radix of 25.

Returning to FIG. 4, the luminescent display 62 which indicates the number of film frames comprises a film frame detecting switch $SW_1$, resistor $R_{24}$, capacitor $C_9$ which prevents a chattling, a waveform shaping buffer inverter $IN_1$, a film frame counter 64, a diode assembly 37B having 7-segment light emitting diodes and which form a display for the number of film frames, another diode assembly 30B having 7-segment light emitting diodes and which form a light emitter assembly used for the entry of the number of film frames, and a decoder/driver 65 associated with the assemblies 37B, 30B. The detecting switch $SW_1$ is adapted to be closed whenever one frame of the film is wound up, and is connected across the feed lines 24a, 24b in series with resistor $R_{24}$. The junction between the switch $SW_1$ and resistor $R_{24}$ is connected through capacitor $C_9$ to the feed line 24b, and is also connected to the input of inverter $IN_1$, the output of which is connected to the counter 64. The counter 64 and the decoder/driver 65 is connected across the feed lines 24a, 24b, and are coupled together by four lines which transmits a BCD (binary coded decimal) code. The decoder/driver 65 is coupled with the diode assemblies 37B, 30B through seven lines which control the light emission thereof. As mentioned previously, the diode assembly 30B which is used for the entry of the number of film frames is connected to the collector of the transistor $Q_5$ so as to be energized from the feed line 24a for illumination whenever the transistor $Q_5$ is turned on. The diode assembly 37B which is used to indicate the number of frames is directly connected to the feed line 24a, thus normally providing an external luminescent display of the number of film frames outside the camera 3.

In the operation of the luminescent display 62, the switch $SW_1$ is closed as each frame of the film is wound up, and the number of film frames is counted by the counter 64, which transmits the count in a BCD code to the decoder/driver 65. The latter then operate to decode the code, thus driving the diode assemblies 37B, 30B for illumination. However, it should be noted that the assembly 37B is normally driven to provide an external display of the number of frames while the assembly 30B is driven only when the transistor $Q_5$ is turned on for the entry of film frames.

The motor control circuit 23 comprises a decimal counter 66 which controls the timing when a film winding by the motor 12 is to be initiated, a counter 67 having the radix of 25 and which controls the time when a film winding operation is to be terminated, a flipflop 68, resistor $R_{25}$ and transistor $Q_6$ which controls the drive to the motor. The decimal counter 66 and the counter 67 having the radix of 25 are connected across the feed lines 24a, 24b through the synchronizing switch 35, and operate to count a count pulse of 32 Hz which is produced by the digital clock circuit 38 whenever the switch 35 is closed. The output of the decimal counter 66 is connected to the set terminal of the flipflop 68 while the output of the counter 67 is connected to the reset terminal of the flipflop 68, the output of which is connected through resistor $R_{25}$ to the base of the transistor $Q_6$. The transistor $Q_6$ comprises an NPN transistor having its collector connected to the feed line 24a through the motor 22 and its emitter connected to the feed line 24b.

In the operation of the motor control circuit 23, the both counters 66, 67 begin to count the pulses of 32 Hz which are produced by the clock circuit 38 as the synchronizing switch 35 is closed. When the count in the counter 66 reaches 10, it sets the flipflop 68. Thereupon the transistor $Q_6$ is turned on to cause the motor 22 to rotate, initiating a film winding operation. Subsequently when the count in the counter 67 reaches 25, the flipflop 68 is reset to turn the transistor $Q_6$ off, thereby terminating the rotation of the motor 22 and hence a winding of one film frame. It is to be noted that the both counters 66, 67 are energized and the clock circuit 38 supplies a count pulse thereto whenever the synchronizing switch 35 is closed. The purpose of this arrangement is to improve the reliability of the motor control circuit 23 by preventing its malfunctioning.

It is to be noted that while in the block diagram of the electrical circuit of the camera 3 shown in FIG. 2, one coil 26a of the transformer 26 is connected to the superimposition and separator circuit 25 which is in turn connected across the feed lines 24a, 24b, in the electrical circuit of FIG. 4, the coil 26a is directly connected across the feed lines 24a, 24b to serve the function of a superimposition circuit while the function of a separator circuit is achieved by the individual resonance circuits of the signal recovery circuits 29, 31. Coils 69a, 69b are connected across the feed lines 24a, 24b to prevent a flow of a high frequency current through the motor 22 and the remainder of the circuit.

In the electrical circuit of the light source unit 4 shown in FIG. 6, the synchronizing switch close signal recovery circuit 52 comprises a resonance capacitor $C_{10}$, an input coupling capacitor $C_{11}$, an a.c. amplifying operational amplifier $OP_5$, a rectifying diode $D_4$, a smoothing capacitor $C_{12}$, a switching transistor $Q_7$ and resistors $R_{26}$–$R_{31}$. The circuit 52 is constructed substantially in the same manner as the signal recovery circuit 29 shown in FIG. 4, and is connected across supply buses 71a, 71b which are connected to a d.c. power supply circuit 71. The transistor $Q_7$ is of an NPN type and has its collector connected through resistor $R_{31}$ to the bus 71a and also connected to the succeeding sequence control circuit 53, thus representing the output terminal of the signal recovery circuit 52. The capacitance of the capacitor $C_{10}$ is chosen to the frequency $f_2$ of the synchronizing switch close signal which is produced by the signal conversion circuit 36 shown in FIG. 4, and when such signal is applied, the transistor $Q_7$ is turned on to supply a trigger signal of an "L" level to the sequence control circuit 53.

The sequence control circuit 53 comprises three timer circuits $TM_1$–$TM_3$. These timer circuits are connected across the buses 71a, 71b. The input of timer circuit $TM_1$ represents an input of the sequence control circuit 53 and hence is connected to the collector of the transistor $Q_7$. The output of timer circuit $TM_1$ is connected to the input of respective timer circuits $TM_2$ and $TM_3$, and the output of timer circuit $TM_2$ is connected to the signal conversion circuit 54 to be described later while the output of timer circuit $TM_3$ is connected to the shutter release signal conversion circuit 55, the automatic exposure calculation circuit 47 and the supply current control circuit 50, respectively. Timer circuit $TM_1$ controls the time when the shutter release operation and the data entry are to be initiated. Timer circuit $TM_2$ controls the duration utilized for the data entry while timer circuit $TM_3$ controls the duration of the shutter release.

Figure 7:
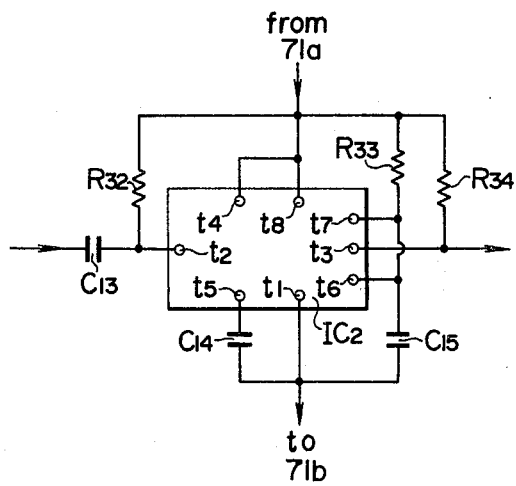
FIG. 7 is a circuit diagram of one form of timer circuit shown in the electrical circuit of FIG. 6.

The timer circuits $TM_1$–$TM_3$ are constructed in an identical manner. One of these circuits is exemplified by a circuit arrangement shown in FIG. 7 wherein it will be noted that the timer circuit is formed by a monostable multivibrator which comprises an integrated circuit $IC_2$ of the type which produces a given time delay and which is commercially available from Hitachi Mfg., Co. as HA17555 or from Signetics Inc. as NE555, three capacitors $C_{13}$–$C_{15}$ and three resistors $R_{32}$–$R_{34}$. The integrated circuit $IC_2$ has eight terminals $t_1$–$t_8$ including a ground (GND), trigger, output, reset, control voltage, threshold, discharge and supply (Vcc) terminal. Trigger terminal $t_2$ is connected with one end of a differentiating capacitor $C_{13}$, the other end of which represents the input of the timer circuit. The trigger terminal is also connected to the bus 71a through a differentiating resistor $R_{32}$ which forms a differentiator together with the capacitor $C_{13}$. The output terminal $t_3$ represents the output of the timer circuit for connection with a succeeding circuit, and is connected through resistor $R_{34}$ to the bus 71a. The reset terminal $t_4$ is connected to the bus 71a together with the supply terminal $t_8$. The control voltage terminal $t_5$ is connected through stabilizing capacitor $C_{14}$ to the bus 71b while the threshold terminal $t_6$ is connected through a timing capacitor $C_{15}$ to the bus 71b. Finally, the discharge terminal $t_7$ is connected through a timing resistor $R_{33}$ to the bus 71a. The both terminals $t_6$ and $t_7$ are connected with each other. It will be noted that the ground terminal $t_1$ is connected to the bus 71b.

In operation, when a negative trigger pulse is applied to the trigger terminal $t_2$, the output is driven to an "H" level, whereby the capacitor $C_{15}$ is charged with a time constant determined by its combination with resistor $R_{33}$. When the voltage across capacitor $C_{15}$ reaches a threshold voltage, it discharges, returning the output to an "L" level.

Returning to FIG. 6, the signal conversion circuit 54 comprises a power amplifier transistor $Q_8$, an oscillation operational amplifier $OP_6$, a switching transistor $Q_9$, resistors $R_{35}$–$R_{40}$ and capacitor $C_{16}$. The transistor $Q_8$ is of an NPN type and has its collector connected through the coil 45a of the transformer 45 to the emitter of the switching transistor $Q_9$. The transistor $Q_8$ has its emitter connected to the bus 71b and its base connected through resistor $R_{35}$ to the output of the operational amplifier $OP_6$. The operational amplifier $OP_6$ is connected across the buses 71a, 71b, and has its inverting input connected through resistor $R_{36}$ to its output and also connected through capacitor $C_{16}$ to the bus 71b. The non-inverting input of the operational amplifier $OP_6$ is connected through resistor $R_{37}$ to its output and also connected to the junction between resistors $R_{39}$ and $R_{38}$ which are connected in series across the buses 71a, 71b. The switching transistor $Q_9$ is of an NPN type, and has its collector connected to the bus 71a. This transistor has its emitter connected to one end of the coil 45d and its base connected through resistor $R_{40}$ to the output of timer circuit $TM_2$.

In the operation of the signal conversion circuit 54, when timer circuit $TM_2$ produces an operating signal of an "H" level for the light emitter assembly, the switching transistor $Q_9$ is turned on, whereby the bus 71a is connected to the collector of the transistor $Q_8$, causing the transistor $Q_8$ to turn on and off repeatedly with an oscillation frequency $f_4$ which is determined by the oscillator of the operational amplifier $OP_6$. In this manner, the operating signal modulates a high frequency so as to be outputted to the coil 45d of the transformer 45.

The shutter release signal conversion circuit 55 comprises a power amplifier transistor $Q_{10}$, an oscillation operational amplifier $OP_7$, a switching transistor $Q_{11}$, resistors $R_{41}$–$R_{46}$ and capacitor $C_{17}$. The circuit 55 is constructed in an identical manner as the conversion circuit 54, and operates to receive a shutter release signal from timer circuit $TM_3$ for modulating a high frequency $f_1$ with this signal, which is then outputted to the coil 45e of the transformer 45.

The automatic exposure signal recovery circuit 46 comprises a resonance capacitor $C_{18}$, an input coupling capacitor $C_{19}$, an a.c. amplifying operational amplifier $OP_8$, full wave rectifying operational amplifiers $OP_9$, $OP_{10}$, feedback diodes $D_5$, $D_6$ and resistors $R_{47}$–$R_{57}$. The resonance capacitor $C_{18}$ is connected in shunt with one of coils, 45b, of the transformer 45, and has its one end connected to one end of the input coupling capacitor $C_{19}$ and has its other end connected to the bus 71b. The other end of the input coupling capacitor $C_{19}$ is connected to the junction between resistors $R_{47}$, $R_{48}$ which are connected in series across the buses 71a, 71b. The junction is also connected to a noninverting input of the operational amplifier $OP_8$, which is connected across the bus 71a and bus 72b which is connected to a negative d.c. power supply circuit 72. Its inverting input is connected through resistor $R_{49}$ to the bus 71b. Another bus 72a connected to the negative d.c. power supply circuit 72 is connected in common with the bus 71b. The output of the operational amplifier $OP_8$ is connected through resistor $R_{50}$ to its inverting input, and is also connected through resistor $R_{52}$ to the inverting input of the operational amplifier $OP_9$ and also connected through resistor $R_{51}$ to the inverting input of the operational amplifier $OP_{10}$. The operational amplifiers $OP_9$ and $OP_{10}$ form a full wave rectifier of well known form, and the non-inverting input of the operational amplifier $OP_9$ is connected through resistor $R_{53}$ to the bus 71b. The output of the operational amplifier $OP_9$ is connected to its inverting input through a forwardly poled diode $D_5$, and is also connected to the inverting input of the operational amplifier $OP_{10}$ through a combination of diode $D_6$ and resistor $R_{55}$. The junction between diode $D_6$ and resistor $R_{55}$ is connected through resistor $R_{54}$ to the inverting input of the operational amplifier $OP_4$. The non-inverting input of the operational amplifier $OP_{10}$ is connected through resistor $R_{56}$ to the bus 71b, and its output is connected through resistor $R_{57}$ to its non-inverting input. It also represents the output terminal of the signal recovery circuit 46.

In the operation of the signal recovery circuit 46, an automatic exposure signal which modulates a frequency $f_3$ which is produced by the signal conversion circuit 34 of the camera 3 is picked up by a resonance circuit formed by the coil 45b of the transformer 45 and capacitor $C_{18}$. The signal is amplified by the operational amplifier $OP_8$, and is then rectified by the full wave rectifier formed by the pair of operational amplifiers $OP_9$ and $OP_{10}$ before it is applied to the succeeding automatic exposure calculation circuit 47. In the full wave rectifier mentioned above, the parameters of the operational amplifier $OP_9$ are chosen so that a negative output voltage is maintained with a gain of unity, and because diode $D_5$ is connected in series in the feedback path, it does not respond to a negative input signal. The operational amplifier $OP_{10}$ is constructed to define an adder which provides a gain of 2 to an output from the operational amplifier $OP_9$ and which provides a gain of unity to an input signal which is fed through resistor $R_{51}$. Consequently, when a positive input signal is applied, twice the inverted output of the operational amplifier $OP_9$ is added to the input voltage, which is then inverted to provide a positive output. Conversely, when a negative input signal is applied, the input voltage is directly inverted and amplified, providing also a positive output. In this manner, an a.c. input signal is subjected to a full wave rectification.

The automatic exposure calculation circuit 47 which receives an output from the signal recovery circuit 46 comprises an integrating, operational amplifier $OP_{11}$, an integrating capacitor $C_{20}$, a photocoupler $PC_1$ which triggers the integration, a transistor $Q_{12}$ which controls a drive to the photocoupler, a comparison operational amplifier $OP_{12}$, a transistor $Q_{13}$ which controls a drive to the electromagnet, and resistors $R_{58}$–$R_{63}$. The output of the signal recovery circuit 46 is connected through resistor $R_{58}$ to the inverting input of the operational amplifier $OP_{11}$, which is connected across the buses 71a, 72b. The operational amplifier $OP_{11}$ has its non-inverting input connected to the bus 71b and its output connected through capacitor $C_{20}$ to its inverting input and also connected through resistor $R_{60}$ to the inverting input of the operational amplifier $OP_{12}$. The photocoupler $PC_1$ includes a photoelectric transducer element which is connected across the inverting input and the output of the operational amplifier $OP_{11}$, and also includes a light emitting element which is connected in series with resistor $R_{59}$ and transistor $Q_{12}$ across the buses 71a, 71b. The transistor $Q_{12}$ is of a PNP type, and has its emitter connected to resistor $R_{59}$ and its collector connected to the bus 71b. The base of the transistor $Q_{12}$ is connected through resistor $R_{61}$ to the output of timer circuit $TM_3$ in the sequence control circuit 53. The operational amplifier $OP_{12}$ is connected across the buses 71a, 72b, and has its inverting input connected through resistor $R_{62}$ to the bus 71a and has its non-inverting input connected to the bus 71b. The output of the operational amplifier $OP_{12}$ is connected through resistor $R_{63}$ to the base of transistor $Q_{13}$, and is also connected through resistor $R_{64}$ to the base of a switching transistor $Q_{14}$ which is contained in the supply current control circuit 50, to be described later. The transistor $Q_{13}$ is of an NPN type, and has its collector connected through the electromagnet assembly 49 to the bus 71a and its emitter connected to the bus 71b.

In the operation of the automatic exposure calculation circuit 47, a shutter release signal produced by timer circuit $TM_3$ of the sequence control circuit 53 turns transistor $Q_{12}$ off, whereby the light emitting element in the photocoupler $PC_1$ ceases to emit light, allowing an integrator formed by the operational amplifier $OP_{11}$ and capacitor $C_{20}$ to initiate integrating an automatic exposure signal which is supplied by the signal recovery circuit 46. When the integrated value reaches a given value, the operational amplifier $OP_{12}$ which is configured as a comparator has its output reversed to an "H" level, whereby transistor $Q_{13}$ is turned on to energize the electromagnet assembly 49. The diaphragm mechanism 48 is then driven to cover the light 51. At the same time, the output of the operational amplifier $OP_{12}$ causes a switching operation to take place within the supply current control circuit 50, reducing the brightness level of light emitted by the light 51.

The supply current control circuit 50 comprises the switching transistor $Q_{14}$, current amplifying transistors $Q_{15}$, $Q_{16}$ and resistors $R_{64}$–$R_{68}$. The transistor $Q_{14}$ is of an NPN type, and has its base connected through resistor $R_{64}$ to the output of the operational amplifier $OP_{12}$, as mentioned previously. The collector of transistor $Q_{14}$ is connected through resistor $R_{65}$ to the output of timer circuit $TM_3$ in the sequence control circuit 53. Both transistors $Q_{15}$ and $Q_{16}$ are of an NPN type, and are connected together in a Darlington configuration. Specifically, transistor $Q_{15}$ has its base connected to the output of timer circuit $TM_3$ and also connected through resistor $R_{66}$ to the emitter thereof. The transistor $Q_{15}$ has its collector connected to the collector of the other transistor $Q_{16}$, and its emitter connected through resistor $R_{67}$ to the bus 71b and also connected to the base of the transistor $Q_{16}$. The transistor $Q_{16}$ has its collector connected through resistor $R_{68}$ to the bus 71b and also connected through the light 51 to a bus 73a which is connected to a light source d.c. power supply circuit 73. Another bus 73b is connected to the circuit 73, and is connected in common with the bus 71b. It will be noted that the emitter of the transistor $Q_{16}$ is connected to the bus 71b.

In the operation of the supply current control circuit 50, the output of timer circuit $TM_3$ normally assumes an "L" level, and hence the both transistors $Q_{15}$, $Q_{16}$ are off. Accordingly, an illumination current from the power supply circuit 73 flows through current controlling resistor $R_{68}$ to the light 51, which therefore exhibits a reduced level of brightness. At a given time interval after the closure of the synchronizing switch 35 (see FIG. 4), a shutter release signal of an "H" level is produced at the output of timer circuit $TM_3$, whereupon the both transistors $Q_{15}$, $Q_{16}$ are turned on to connect the collector-emitter path of the transistor $Q_{16}$ in shunt with resistor $R_{68}$, since the "L" level output of the operational amplifier $OP_{12}$ maintains the transistor $Q_{14}$ off. Consequently, an increased current flows through the light 51, causing it to exhibit an increased level of brightness. When the operational amplifier $OP_{12}$ reverses to return its output level to an "H" level, transistor $Q_{14}$ is turned on, whereby the transistors $Q_{15}$, $Q_{16}$ are turned off, restoring the current level supplied to the light 51 to its original value.

Figure 8:
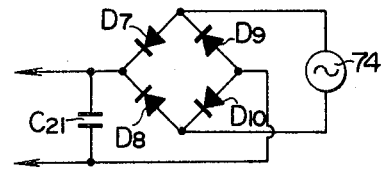
FIG. 8 is a circuit diagram of one form of a d.c. power supply shown in the electrical circuit of FIG. 6.

The d.c. power supply circuits 42, 71–73 are formed by a single phase full wave rectifier as shown in FIG. 8 which rectifies an alternating current from an a.c. supply 74 into direct current. Specifically, the rectifier comprises a bridge formed by four rectifying diodes $D_7$–$D_{10}$ and smoothing capacitor $C_{21}$. The junction between diodes $D_7$ and $D_9$ and the junction between diodes $D_8$ and $D_{10}$ are connected across the a.c. supply 74. The junction between diodes $D_7$ and $D_8$ and the junction between diodes $D_9$ and $D_{10}$ are connected with a pair of supply buses across which the smoothing capacitor $C_{21}$ is connected. Obviously, the rectifier converts an a.c. output from the supply 74 into direct current.

Although in the block diagram of the light source unit 4 shown in FIG. 3, the superimposition and separator circuit 44 is connected to the coil 45a of the transformer 45 and is also connected with the feed line 43a, 43b, in the circuit arrangement shown in FIG. 6, the superimposition and separator circuit is formed by the respective coils 45a–45e of the transformer 45, and a smoothing circuit comprising a pair of smoothing coils 75a, 75b connected in series in the feed lines 43a, 43b, respectively, in order to prevent an adverse influence of the high frequency signal upon the supply circuit 42.

Figure 9:
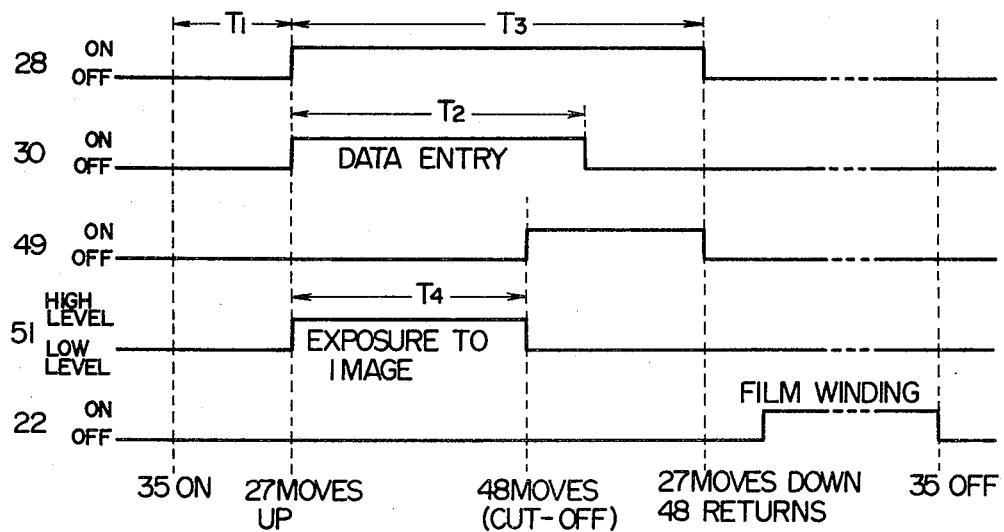
FIG. 9 is a timing chart illustrating the operation of the apparatus of the invention.

Having described the arrangement of the specific electrical circuits of the camera 3 and the light source unit 4, their operation will now be described below in connection with the operation of the apparatus for endoscopic photography with reference to a timing chart shown in FIG. 9.

Initially, when a shutter release button is depressed to close the synchronizing switch, the signal conversion circuit 36 is energized, and the oscillator circuit formed by the operational amplifier $OP_2$ begins to oscillate at the frequency $f_2$, outputting a synchronizing switch close signal modulated on a high frequency carrier signal to the coil 26e. The close signal is transmitted to the light source unit 4 through the feed lines 12a, 12b of the endoscope 2, and the signal recovery circuit 52 is tuned to this frequency, turning transistor $Q_7$ on, whereby timer circuit $TM_1$ of the sequence control circuit 53 produces an output of "H" level for a timer interval $T_1$. Simultaneously the close signal is applied to the digital clock circuit 38 of the luminescent display 61, feeding count pulses of 32 Hz to the counters 66 and 67, which are then fed from the supply buses to begin their counting operation.

After the time interval $T_1$ has passed, the output of timer circuit $TM_1$ returns to "L" level, thus triggering succeeding timer circuits $TM_2$ and $TM_3$. Accordingly, the outputs of these timer circuits go high or assumes "H" level. The output of timer circuit $TM_2$ turns transistor $Q_9$ in the signal conversion circuit 54 on, causing the oscillation circuit formed by the operational amplifier $OP_6$ to oscillate at the frequency $f_4$. In this manner, an operating signal for the light emitter assembly which modulates the high frequency carrier signal is supplied to the coil 45d of the transformer 45 for transmission to the camera 3. In the camera 3, the signal recovery circuit 31 is tuned to the frequency carrier signal, whereby transistor $Q_5$ is turned on to connect the light emitting diode elements 30a–30f of the luminescent display 61 which indicates a photographing date as well as the diode assembly 30B of the luminescent display 62 which indicates the number of film frames to the feed line 24a, allowing these elements of the assembly to emit light to thereby initiate the data entry.

On the other hand, the output of timer circuit $TM_3$ is supplied to the shutter release signal conversion circuit 55, the automatic exposure calculation circuit 47 and the supply current control circuit 50. The signal conversion circuit 55 responds to the output from timer circuit $TM_3$ by turning transistor $Q_{11}$ on, whereby the oscillator circuit formed by the operational amplifier $OP_7$ oscillates at the frequency $f_1$, supplying the oscillation output to the transformer 45 as a shutter release signal. In the camera 3, the shutter release signal recovery circuit 29 is tuned to this frequency, whereby transistor $Q_1$ is turned on to energize the electromagnet assembly 28. In response thereto, the mirror shutter 27 is driven to move up, beginning the exposure of the film to an image of an object being photographed. In the automatic exposure calculation circuit 47, transistor $Q_{12}$ is turned on by the output from timer circuit $TM_3$, allowing the light emitting elements in the photocoupler $PC_1$ to emit light. Then the integrator circuit formed by the operational amplifier $OP_{11}$ begins integrating the automatic exposure signal supplied from the signal recovery circuit 46.

In the supply current control circuit 50, the output from timer circuit $TM_3$ turns transistors $Q_{15}$, $Q_{16}$ on, whereby the current flow fed to the light 51 increases. Consequently, the light 51 exhibits an increased level of brightness. The resulting light emitted by the light 51 is fed through the light guide or the bundle of the optical fibres 9 to irradiate the internal wall 5 of a coeliac cavity. The light is reflected by the wall 5 and transmitted through the image guide or the bundle of optical fibres 8 to the camera 3, causing an exposure of the film surface to the image of an object being photographed. Part of the incident light impinges on the photometric element 33 which is utilized for the purpose of determining an automatic exposure period, and the element 33 produces a photocurrent having a magnitude which depends on the brightness of the image. The photocurrent is d.c. amplified by the operational amplifier $OP_4$ and is then fed to the multiplier circuit $IC_1$ where it is superimposed on the oscillation output of frequency $f_3$ produced by the operational amplifier $OP_{3b}$ for output to the transformer 26. In the light source unit 4, the automatic exposure signal recovery circuit 46 is tuned to the frequency which is amplitude modulated by the photocurrent or the automatic exposure signal, and which is amplified by the operational amplifier $OP_8$. Subsequently, it is subject to a full wave rectification by the rectifier formed by the operational amplifiers $OP_9$, $OP_{10}$, whereby it is demodulated. Demodulated automatic exposure signal is supplied to the automatic exposure calculation circuit 47, and is integrated by the integrator circuit formed by the operational amplifier $OP_{11}$.

When the exposure of the film surface has reached a proper value after a time interval $T_4$ has passed since the upward movement of the mirror shutter 27, the output voltage of the operational amplifier $OP_{11}$ exceeds a given level, whereby it reverses, turning transistors $Q_{13}$ and $Q_{14}$ on. As the transistor $Q_{13}$ is turned on, the electromagnet assembly 49 is energized to drive the diaphragm mechanism 48, thus interrupting the passage of the light from the light 51 to the light guide 9. Thus, no light irradiates the internal wall 5, terminating the exposure of the film. At the same time, as the transistor $Q_{14}$ is turned on, transistors $Q_{15}$, $Q_{16}$ are turned off, returning the illumination level of the light 51 from its photographing, high brightness level to its low brightness, observation level.

After a time interval of $T_2$, the output of timer circuit $TM_2$ changes to "L" level, whereby transistor $Q_9$ is turned off and the signal conversion circuit 54 ceases to produce an operating signal associated with light emitter assembly. Hence, there is no input to the signal recovery circuit 31, turning transistor $Q_5$ off. Hence, the emission of light by diode elements $30a$–$30f$, $30B$ is interrupted, completing the data entry.

After a time interval $T_3$ has passed, the output of timer circuit $TM_3$ changes to "L" level, whereby transistor $Q_{11}$ is turned off and the signal conversion circuit 55 ceases to produce the shutter release signal. Hence, there is no input signal to the signal conversion circuit 29, so that transistor $Q_1$ is turned off, deenergizing the electromagnet assembly 28. Thus, the mirror shutter is allowed to return to its position located on the taking light path. As the output of timer circuit $TM_3$ reverts to "L" level, transistors $Q_{13}$, $Q_{14}$ are turned off. When transistor $Q_{13}$ is turned off, the electromagnet assembly 49 is deenergized, retracting the diaphragm mechanism 48 from its light shielding position. Hence, the light from the light 51 which is passed through the light guide 9 irradiates the internal wall 5, permitting an observation of the coeliac cavity.

Subsequently, when the decimal counter 66 in the motor control circuit 23 has counted ten count pulses from the clock circuit 38, it produces a set pulse which is applied to the flipflop 68, causing it to provide an "H" level output. Accordingly, transistor $Q_6$ is turned on to drive the film winding d.c. motor 22, initiating a film winding operation. Subsequently when the counter 67 has counted 25 count pulses from the clock circuit 38, it produces a reset pulse which is applied to the flipflop 68, causing it to produce an "L" level output. This turns transistor $Q_6$ off to stop the motor 22, terminating a film winding operation after one film frame has been wound up. In interlocked relationship with the film winding operation, a charging operation for enabling an upward movement of the mirror shutter is effected and the synchronizing switch 35 is opened.

In this manner, a series of operations including an upward movement of the mirror shutter, the exposure of the film surface to an image of an object being photographed, data entry, downward movement of the mirror shutter and the film winding which are required to take a single picture are automatically performed.

What is claimed is:

1. An apparatus for endoscopic photography in which a camera is mounted on an endoscope and a light source unit is connected to the endoscope and a film winding d.c., motor located within the camera is interconnected with a d.c. power supply circuit located within said light source unit through d.c. feed lines disposed within said endoscope; said apparatus comprising:

a signal conversion circuit for modulating a high frequency carrier signal with a first signal, and a superimposed circuit for superimposing said modulated high frequency signal on a d.c. signal and for placing said superimposed signal on said d.c. feed line, said signal conversion circuit and said superimposition circuit being located in one of said camera and said light source unit;

a separator circuit coupled to said d.c. feed lines for separating said modulated high frequency signal from said d.c. signal, and a signal recovery circuit for receiving and demodulating said separated modulated high frequency signal so as to recover said first signal, said separator circuit and said signal recovery circuit being disposed in the other of said camera and said light source unit, thereby allowing a communication of said first signal between said camera and said light source unit through the d.c. feed lines.

2. An apparatus according to claim 1, in which said signal conversion circuit comprises a synchronizing switch close signal conversion circuit connected to a synchronizing switch which is disposed within said camera, and in which said signal recovery circuit comprises a synchronizing switch close signal recovery circuit connected to a sequence control circuit which is disposed within said light source unit.

3. An apparatus according to claim 1 in which said signal conversion circuit comprises an automatic exposure signal conversion circuit connected to a photoelectric transducer element disposed within said camera to effect photometry for automatic exposure control, and in which said signal recovery circuit comprises an automatic exposure signal recovery circuit connected to an automatic exposure calculation circuit which is disposed within said light source unit.

4. An apparatus according to claim 1 in which said signal conversion circuit comprises a signal conversion circuit for an operating signal associated with a light emitter assembly, said conversion circuit being connected to a sequence control circuit disposed within said light source unit, and in which said signal recovery circuit comprises a signal recovery circuit connected to said light emitter assembly disposed within said camera for recovering said operating signal associated with said light emitter assembly.

5. An apparatus according to claim 1 in which said signal conversion circuit comprises a shutter release signal conversion circuit connected to a sequence control circuit disposed within said light source unit, and in which said signal recovery circuit comprises a shutter release signal recovery circuit connected to a shutter release electromagnet assembly disposed within said camera.

6. An apparatus according to claim 1, in which said superimposition circuit comprises a coupling coil of a coupling transformer connected to said high frequency signal conversion circuit, and another coupling coil of said transformer connected to the feed line.

7. An apparatus according to claim 1, in which said separator circuit comprises a coupling coil of a coupling transformer which is connected to said signal recovery circuit, and a resonance capacitor connected to said signal recovery circuit in shunt with said coupling coil.

8. An apparatus according to claim 1, in which there are provided a plurality of sets of said signal conversion circuits and said signal recovery circuits, each set being responsive to a frequency band which is different from the frequency bands to which other sets respond.

* * * * *